(12) United States Patent
Brown

(10) Patent No.: US 9,400,241 B2
(45) Date of Patent: *Jul. 26, 2016

(54) SOLUTE CONCENTRATION MEASUREMENT DEVICE AND RELATED METHODS

(71) Applicant: Tandem Diabetes Care, Inc., San Diego, CA (US)

(72) Inventor: David Brown, Carlsbad, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 178 days.

This patent is subject to a terminal disclaimer.

(21) Appl. No.: 14/166,327

(22) Filed: Jan. 28, 2014

(65) Prior Publication Data
US 2014/0137641 A1    May 22, 2014

Related U.S. Application Data

(62) Division of application No. 12/563,046, filed on Sep. 18, 2009, now Pat. No. 8,650,937.

(60) Provisional application No. 61/098,655, filed on Sep. 19, 2008, provisional application No. 61/102,776, filed on Oct. 3, 2008.

(51) Int. Cl.
*G01N 13/04* (2006.01)
*G01N 1/40* (2006.01)

(52) U.S. Cl.
CPC .............. *G01N 13/04* (2013.01); *G01N 1/4055* (2013.01); *G01N 2001/4061* (2013.01)

(58) Field of Classification Search
CPC ................ G01N 1/4055; G01N 13/04; G01N 2001/4061
USPC .......................................... 73/64.47; 600/365
See application file for complete search history.

(56) References Cited

U.S. PATENT DOCUMENTS 3,187,562 A    6/1965    Rolfson
3,318,138 A    5/1967    Rolfson
(Continued)

FOREIGN PATENT DOCUMENTS

JP    2952037    9/1999
KR    10-0525720    11/2005
(Continued)

OTHER PUBLICATIONS

EP Search Report, Application No. 09815314.1-1553-2334234 mailed Feb. 18, 2013.
(Continued)

*Primary Examiner* — Daniel S Larkin
(74) *Attorney, Agent, or Firm* — Patterson Thuente Pederson, P.A.

(57) ABSTRACT

A solute concentration measurement device is disclosed. The device may comprise a filter membrane, an exchange chamber, a sensing chamber, a separator, and a sensor. The device may be configured to be placed in fluid communication with a sample solution containing a solute and a solvent. The filter membrane may provide selective fluid communication between the solution and the exchange chamber. The separator may separate the exchange chamber from the sensing chamber and cause a change in a condition of the sensing chamber corresponding to a change of a condition of the exchange chamber. The sensor may sense the condition pertaining to the sensing chamber and calculate the concentration of the sample solution corresponding to this change.

20 Claims, 3 Drawing Sheets

(56) References Cited

U.S. PATENT DOCUMENTS

| | | | |
|---|---|---|---|
| 3,455,147 A | 7/1969 | Peck et al. |
| 4,028,931 A | 6/1977 | Bisera et al. |
| 4,403,984 A | 9/1983 | Ash et al. |
| 4,445,885 A | 5/1984 | Kifune |
| 4,481,808 A | 11/1984 | Sakata et al. |
| 4,538,616 A | 9/1985 | Rogoff |
| 4,622,974 A | 11/1986 | Coleman et al. |
| 4,718,430 A | 1/1988 | Holzer |
| 5,005,403 A | 4/1991 | Steudle et al. |
| 5,211,055 A * | 5/1993 | Steudle ................ G01N 13/04 73/64.47 |
| 5,337,747 A | 8/1994 | Neftel |
| 5,527,288 A | 6/1996 | Gross et al. |
| 5,848,991 A | 12/1998 | Gross et al. |
| 5,871,125 A | 2/1999 | Gross |
| 5,997,501 A | 12/1999 | Gross et al. |
| 6,048,337 A | 4/2000 | Svedman |
| 6,074,359 A | 6/2000 | Keshaviah et al. |
| 6,091,976 A | 7/2000 | Pfeiffer et al. |
| 6,120,460 A | 9/2000 | Abreu |
| 6,268,161 B1 * | 7/2001 | Han .................... A61B 5/0031 435/14 |
| 6,360,888 B1 | 3/2002 | McIvor et al. |
| 6,391,643 B1 | 5/2002 | Chen et al. |
| 6,436,078 B1 | 8/2002 | Svedman |
| 6,475,750 B1 | 11/2002 | Han et al. |
| 6,489,346 B1 | 12/2002 | Phillips |
| 6,514,689 B2 | 2/2003 | Han et al. |
| 6,520,936 B1 | 2/2003 | Mann |
| 6,558,351 B1 | 5/2003 | Steil et al. |
| 6,572,566 B2 | 6/2003 | Effenhauser |
| 6,584,335 B1 | 6/2003 | Haar et al. |
| 6,699,885 B2 | 3/2004 | Phillips |
| 6,881,551 B2 | 4/2005 | Heller et al. |
| 6,892,085 B2 | 5/2005 | McIvor et al. |
| 7,008,403 B1 | 3/2006 | Mallett |
| 7,163,520 B2 | 1/2007 | Bernard et al. |
| 7,276,028 B2 | 10/2007 | Ellingsen et al. |
| 7,341,581 B2 | 3/2008 | Mallett |
| 7,348,176 B2 | 3/2008 | DiMilla et al. |
| 7,374,556 B2 | 5/2008 | Mallett |
| 7,399,772 B2 | 7/2008 | Phillips |
| 7,445,616 B2 | 11/2008 | Petrakis |
| 7,459,305 B2 | 12/2008 | Levy |
| 7,496,392 B2 | 2/2009 | Alarcon et al. |
| 7,514,075 B2 | 4/2009 | Hedrick et al. |
| 7,591,801 B2 | 9/2009 | Brauker et al. |
| 7,657,297 B2 | 2/2010 | Simpson et al. |
| 7,687,272 B1 | 3/2010 | Buchwald et al. |
| 7,749,528 B2 | 7/2010 | De Carvalho et al. |
| 7,774,145 B2 | 8/2010 | Brauker et al. |
| 7,976,492 B2 | 7/2011 | Brauker et al. |
| 8,016,740 B2 | 9/2011 | Connors et al. |
| 8,071,075 B2 | 12/2011 | Reed et al. |
| 8,105,265 B2 | 1/2012 | Demers et al. |
| 8,114,350 B1 | 2/2012 | Silver et al. |
| 8,372,040 B2 | 2/2013 | Huang et al. |
| 8,460,231 B2 | 6/2013 | Brauker et al. |
| 8,562,558 B2 | 10/2013 | Kamath et al. |
| 8,650,937 B2 | 2/2014 | Brown |
| 2003/0208113 A1 | 11/2003 | Mault et al. |
| 2005/0154272 A1 | 7/2005 | Dirac et al. |
| 2006/0022051 A1 | 2/2006 | Patel et al. |
| 2006/0076236 A1 | 4/2006 | Shah et al. |
| 2007/0227907 A1 | 10/2007 | Shah et al. |
| 2007/0264130 A1 | 11/2007 | Mallett |
| 2008/0026473 A1 | 1/2008 | Wang et al. |
| 2008/0058697 A1 | 3/2008 | Kamen et al. |
| 2008/0071220 A1 | 3/2008 | Rhinehart et al. |
| 2008/0306434 A1 | 12/2008 | Dobbles et al. |
| 2008/0306444 A1 | 12/2008 | Brister et al. |
| 2009/0191067 A1 | 7/2009 | DiPerna |
| 2009/0192724 A1 | 7/2009 | Brauker et al. |
| 2010/0071446 A1 | 3/2010 | Brown |
| 2010/0114027 A1 | 5/2010 | Jacobson et al. |
| 2010/0121169 A1 | 5/2010 | Petisce et al. |
| 2010/0179402 A1 | 7/2010 | Goode, Jr. et al. |
| 2010/0256593 A1 | 10/2010 | Yodfat et al. |
| 2010/0280486 A1 | 11/2010 | Khair et al. |
| 2011/0257895 A1 | 10/2011 | Brauker et al. |
| 2012/0123230 A1 | 5/2012 | Brown et al. |

FOREIGN PATENT DOCUMENTS

| | | |
|---|---|---|
| WO | WO 99/01088 | 1/1999 |
| WO | WO9917095 | 4/1999 |
| WO | WO 2008/037272 | 4/2008 |
| WO | WO 2009/006419 | 1/2009 |
| WO | WO2011014704 | 2/2011 |

OTHER PUBLICATIONS

International Search Report and Written Opinion Mailed on Sep. 10, 2004 in International Application: PCT/US2003//022703 filed on Jul. 15, 2003 and published as WO 04/009152 on Jan. 29, 2004.

International Search Report and Written Opinion mailed on: Feb. 4, 2010 in International Application: PCT/2009/049166 filed on: Jun. 29, 2009 and published as: WO 10/016978 on: Feb. 11, 2010.

International Search Report and Written Opinion mailed on: Jul. 28, 2009 in International Application: PCT/US2009/031906 filed on Jan. 23, 2009 and published as: WO 09/094590 on Jul. 30, 2009.

International Search Report and Written Opinion mailed on: Jan. 4, 2010 in International Application: PCT/US2009/044569 filed on: May 19, 2009 and published as WO 09/143188 on: Nov. 26, 2009.

U.S. Appl. No. 60/789,243, Inventor: Beavis, filed Apr. 5, 2006.

Application and File History for U.S. Appl. No. 13/272,111, filed Oct. 12, 2011 inventors Brown et al.

Application and File History for U.S. Appl. No. 12/563,046, filed Sep. 18, 2009, inventor Brown.

Australian Examination Report No. 1 for Australian Application No. 2009293019 dated May 21, 2014.

* cited by examiner

SOLUTE CONCENTRATION MEASUREMENT DEVICE AND RELATED METHODS

RELATED APPLICATIONS

This application is a division of U.S. patent application Ser. No. 12/563,046, filed Sep. 18, 2009, now U.S. Pat. No. 8,650,937, which claims the Paris Convention Priority of U.S. Provisional Application No. 61/098,655, filed Sep. 19, 2008, and U.S. Provisional Application No. 61/102,776, filed Oct. 3, 2008, all of which are incorporated by reference herein.

BACKGROUND

This disclosure relates generally to devices and methods for determination of an unknown solute concentration in a solution. In particular, the present disclosure relates to determining the concentration of a solute, such as glucose, in the body fluids, such as interstitial fluid or bloodstream, of a patient who requires monitoring of such concentration for medical purposes.

SUMMARY

Briefly stated, a solute concentration measurement device and related methods are disclosed wherein the device is configured to be placed in fluid communication with a solution of initially unknown concentration and may determine the concentration of the solution by allowing selective diffusion of a solvent and by measuring the conditions within the device that are affected by diffusion of the solvent.

According to embodiments, a solute concentration measurement device may comprise, in combination: a filter membrane, an exchange chamber, a sensing chamber, a separator, and a sensor. The device may be configured to be placed in fluid communication with a sample solution containing a solute and a solvent. The filter membrane may provide selective fluid communication between the sample solution and the exchange chamber. The separator may separate the exchange chamber from the sensing chamber and cause a change in a condition of the sensing chamber corresponding to a change of a condition of the exchange chamber. The sensor may sense the condition pertaining to the sensing chamber and calculate the concentration of the sample solution corresponding to this change.

According to embodiments, a solute concentration measurement device may comprise, in combination: an exchange chamber, a sensing chamber, wherein the device is configured to be placed in fluid communication with a sample solution; means for providing selective fluid communication between the sample solution and the exchange chamber; means for separating the exchange chamber from the sensing chamber; means for sensing a condition pertaining to the sensing chamber. The device may further comprise: means for determining a concentration of the sample solution based on the condition pertaining to the sensing chamber According to embodiments, a method for measuring a solute concentration may comprise, in combination: providing a solute concentration measurement device comprising an exchange chamber and a sensing chamber, configured to be placed in fluid communication with a sample solution; providing selective fluid communication between the sample solution and the exchange chamber; separating the exchange chamber from the sensing chamber; sensing a condition pertaining to the sensing chamber. The method may further comprise the step of: determining a concentration of the sample solution based on the condition pertaining to the sensing chamber.

DRAWINGS

The above-mentioned features and objects of the present disclosure will become more apparent with reference to the following description taken in conjunction with the accompanying drawings wherein like reference numerals denote like elements and in which.

Figure 4:
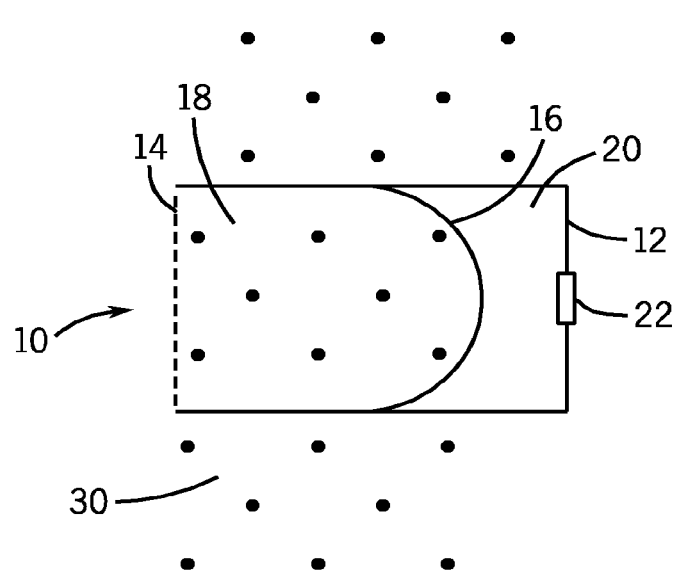
Figure 5:
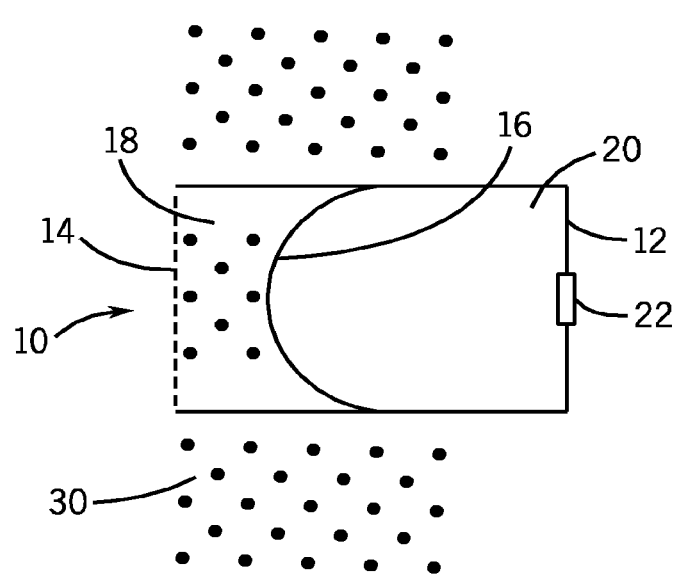

FIG. 4 is a schematic view of an embodiment of a solute concentration measurement device, being placed in fluid communication with a sample solution of low concentration; and FIG. 5 is a schematic view of an embodiment of a solute concentration measurement device, being placed in fluid communication with a sample solution of high concentration, according to one or more embodiments of the present disclosure.

DETAILED DESCRIPTION

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

As used herein, the term "real time" shall be understood to mean the instantaneous moment of an event or condition, or the instantaneous moment of an event or condition plus short period of elapsed time used to make relevant measurements, optional computations, etc., and communicate the measurement, computation, or etc., wherein the state of an event or condition being measured is substantially the same as that of the instantaneous moment irrespective of the elapsed time interval. Used in this context "substantially the same" shall be understood to mean that the data for the event or condition remains useful for the purpose for which it is being gathered after the elapsed time period.

The inventors of the present disclosure have discovered devices and methods for determining the concentration of a solute in a solution in real time. Specifically, the concentration of glucose in the body fluids may be monitored by the devices and using the methods of the present disclosure in real time. The devices disclosed herein, may be long term implantable devices, or devices that connect to ports that allow for fluid communication between the device and body fluids.

Figure 1:
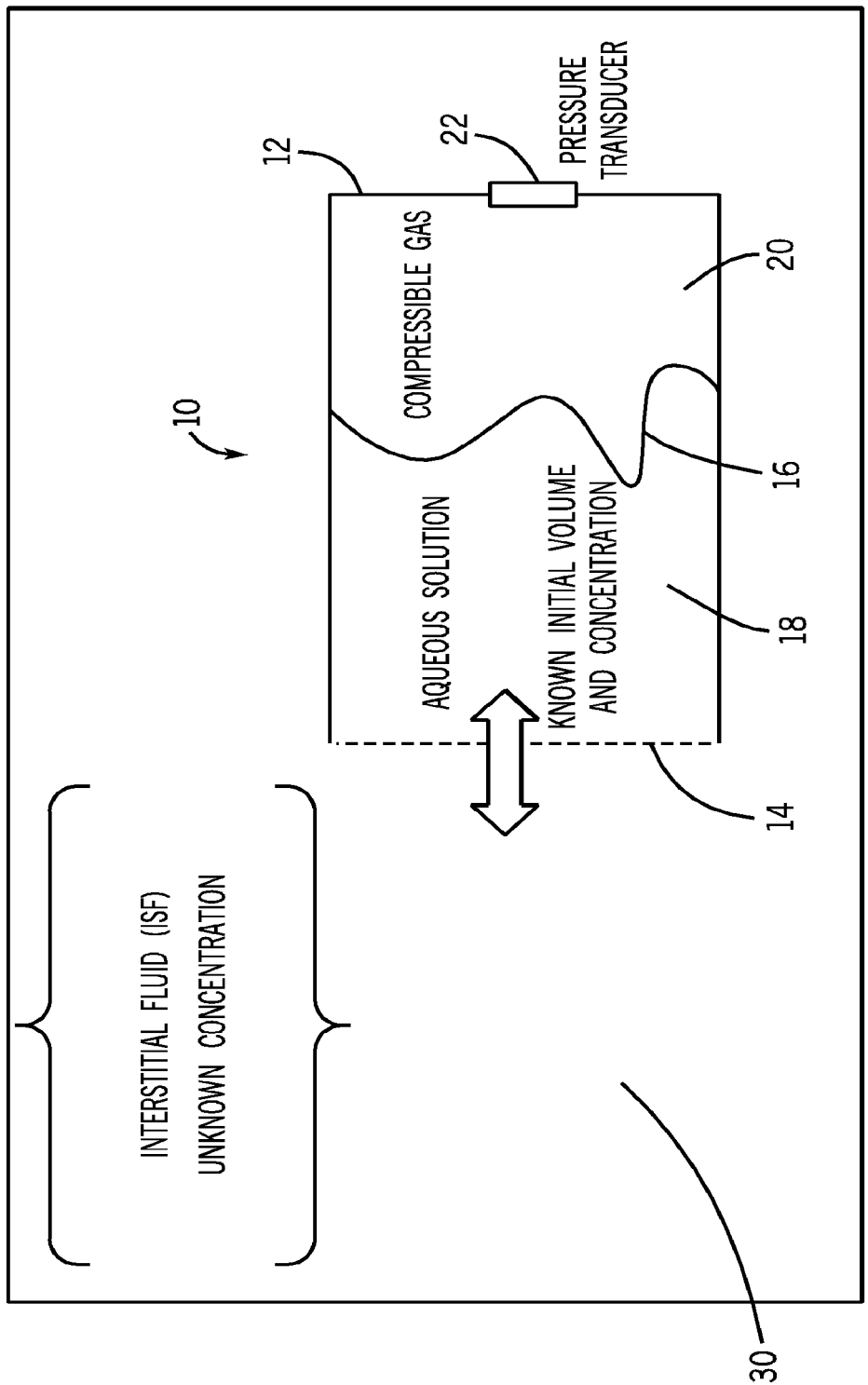
FIG. 1 is a schematic view of an embodiment of a solute concentration measurement device.
Figure 2:
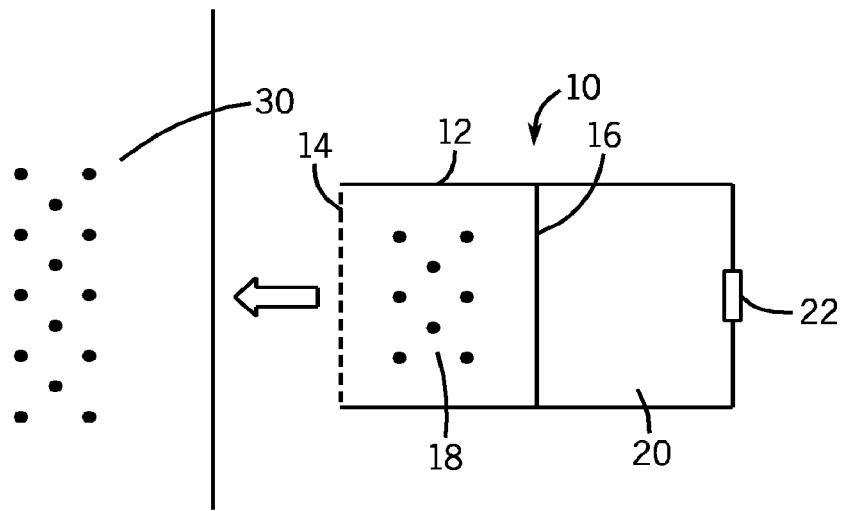
FIG. 2 is a schematic view of an embodiment of a solute concentration measurement device, prior to being placed in fluid communication with a sample solution.
Figure 3:
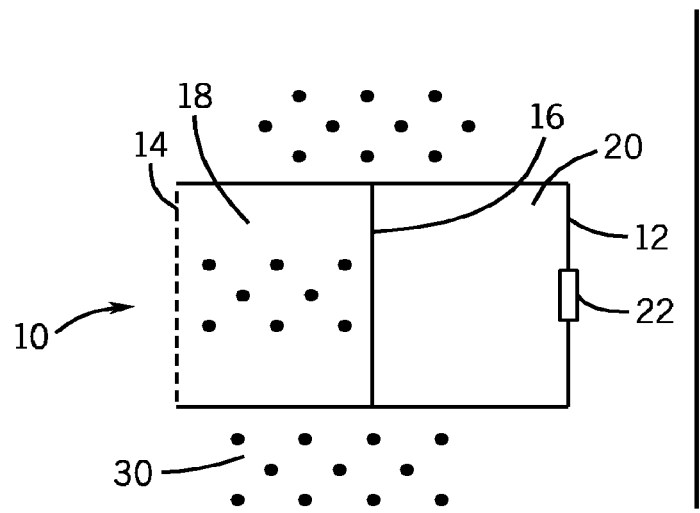
FIG. 3 is a schematic view of an embodiment of a solute concentration measurement device, after being placed in fluid communication with a sample solution.

According to embodiments, FIG. 1 illustrates a solute concentration measurement device 10. When used as a medical device, artisans appreciate the instant system as adjustable and configured to optimally support a patient's needs, as determined by qualified care providers. According to embodiments, device 10 is used to measure the concentration of glucose in a patient's body fluids, such as interstitial fluid or blood, in real-time. FIG. 2 depicts the device 10 prior to being inserted into a sample solution 30 and FIGS. 3-5 depict the device immersed in the sample solution 30, with the solid vertical line in each figure representing a figurative boundary of an area containing the sample solution 30.

According to embodiments, device 10 includes housing 12, which encloses exchange chamber 18 and sensing chamber 20. According to embodiments, at least a portion of housing 12 includes filter membrane 14. Filter membrane 14 may separates exchange chamber 18 from sample solution 30.

According to embodiments, filter membrane 14 provides selective fluid communication between sample solution 30 and exchange chamber 18. For example, filter membrane 14 may be a selectively permeable membrane. According to embodiments, filter membrane 14 may permit unrestricted passage of the solvent of sample solution 30 across filter membrane 14, but prohibit passage of the solutes of sample solution 30 across filter membrane 14. According to embodiments, filter membrane 14 is a thin film composite membrane or osmotic membrane.

According to embodiments, exchange chamber 18 may contain an exchange solution containing at least one solute as are found in sample solution 30. According to embodiments, the solvent that moves across filter membrane 14 is water. Filter membrane 14 allows free exchange of the solvent, but prohibits passage of the solute common to sample solution 30 and exchange chamber 18, thereby retaining the same number of solute molecules in exchange chamber 18 and making possible the calculation of the concentration in exchange chamber 18. According to embodiments, exchange chamber 18 comprises a small volume compared to the volume of sample solution 30 such that the process of equalizing the concentration of exchange chamber 18 will not appreciably change the concentration of sample solution 30.

According to embodiments, separator 16 divides exchange chamber 18 from sensing chamber 20. Generally, separator 16 comprises a device that allows exchange chamber 18 to increase or decrease in volume depending on the volume of solvent in exchange chamber 18. Because the total volume of device 10 is fixed, the volume of exchange chamber 18 is inversely proportional to the volume of sensing chamber 20, as illustrated in FIGS. 3, 4, and 5.

Separator 16 comprises a piston or elastomeric membrane, for example. Artisans will readily recognize devices that sealably separate exchange chamber 18 and sensing chamber 20, while allowing separator 16 to be adjusted whereby the volumes of exchange chamber 18 and sensing chamber 20 are changed. Separator 16 responds to the change in volume of exchange chamber 18 as solvent moves into or out of exchange chamber 18. For example, separator 16 may respond to an increase in the pressure within exchange chamber 18 relative to the pressure within sensing chamber 20 by increasing the volume of exchange chamber 18 and decreasing the volume of sensing chamber 20 until equilibrium of pressures occurs.

According to embodiments, housing 12 is rigid, such that the total combined volume of exchange chamber 18 and sensing chamber 20 is constant. Thus, a change in the volume of exchange chamber 18 results in a corresponding, equal and opposite change in the volume of sensing chamber 20 to maintain the total combined volume of both. Sensing chamber 20 contains a compressible fluid that varies in pressure as a consequence of any change in volume of sensing chamber 20. According to embodiments, sensing chamber 20 contains a compressible gas. The volume and pressure of the gas changes as separator 16 varies in position.

According to embodiments, sensing chamber 20 may include pressure sensor 22. Sensor 22 measures the pressure of the gas in sensing chamber 20. For example, sensor 22 may be a pressure transducer to measure the pressure within sensing chamber 20. According to embodiments, a temperature sensor may also be disposed in sensing chamber 20 to improve the accuracy of the measurement.

According to embodiments, the distance separator 16 travels as it adjusts while exchange chamber 18 comes to equilibrium may be measured, allowing for a determination of the change in volume in sensing chamber 20, thereby allowing the concentration of exchange chamber 18 to be calculated, as disclosed herein.

A computer performs the relevant calculations. The computer comprises at least a timing device for measuring elapsed time, which may comprise a clock or a timer, for example; devices to receive input from the pressure sensors, temperature sensors, and users; and a processor for performing the calculations disclosed herein.

According to embodiments, a method is disclosed herein for measuring the concentration of sample solution 30. Solute concentration measurement device 10 is put in fluid communication with a sample solution 30, whereby at least filter membrane 14 is in fluid communication with sample solution 30. According to embodiments, sample solution 30 includes a solute and a solvent. According to embodiments, sample solution 30 is a fluid within a body of a patient requiring medical treatment relating to the concentration of a solute in sample solution 30. According to embodiments, sample solution 30 comprises interstitial fluid; accordingly glucose is the solute.

The concentrations of sample solution 30 and exchange chamber 18 equalize as the solvent moves across filter membrane 14. Accordingly, the concentrations of sample solution 30 and exchange chamber 18 will reach substantial equilibrium through the diffusion of the solvent across filter membrane 14. According to embodiments, a predetermined time period may need to elapse for the exchange chamber 18 to come into equilibrium with sample solution 30.

According to other embodiments, allowing exchange chamber 18 to come into equilibrium is not necessary. Rather, prior to contact with sample solution 30, one or more curves may be modeled from test sample solutions of known concentration for a given period of time. The results will be a number of curves that illustrate pressure of sensing chamber 20 versus concentration. Consequently, rather than waiting for establishment of equilibrium, the concentration may be determined by fitting the change in concentration of exchange chamber 18 to a curve of known behavior.

According to embodiments, FIG. 4 shows an embodiment of a solute concentration measurement device in a sample solution of lower concentration than exchange chamber 18. When device 10 is placed into fluid communication across filter membrane 14, solvent, for example water, flows across filter membrane 14 until the concentrations of exchange chamber 18 and sample solution 30 is substantially the same.

According to embodiments, the amount of solute in exchange chamber 18 is known. Initially, a known volume of fluid is placed into exchange chamber 18 and a pressure measurement is taken with pressure sensor 22. Thus, the initial concentration of device 10 is determined prior to placing it into contact with sample solution 30.

According to alternate embodiments, the concentration of sample solution 30 is known. Because exchange chamber 18 is separated by filter membrane 14, solvent may eventually cross over the membrane or solvent may be lost, e.g., due to evaporation, whereby an initial calibration no longer accurately represents the concentration of exchange chamber 18.

According to embodiments, recalibration solution may be provided whereby device 10 is recalibrated. The concentration of recalibration solution is known and can be input into device 10. Device 10 is then placed in fluid communication with the recalibration solution across filter membrane 14 and a recalibration command is given before or after the concentrations of recalibration solution and exchange chamber 18 come into equilibrium. If given before, device 10 allows for a time period for equilibrium to occur. After equilibrium occurs, one or more pressure measurements will be taken and device 10 will thereafter have a corrected "base" concentration.

FIG. 5 shows embodiments of device 10 when it is placed in fluid communication of sample solution 30 of higher concentration than that of exchange chamber 18, according to embodiments. Due to the osmotic pressure when placed in fluid communication with sample solution 30 of higher concentration, solvent travels across filter membrane 14 from exchange chamber 18 into sample solution 30 until equilibrium of concentrations is reached. Resultantly, separator is repositioned whereby the volume of exchange chamber 18 is reduced and the volume of sensing chamber 20 is increased. Taking a pressure measurement after equilibrium is established allows for calculation of the concentration of sample solution 30.

According to embodiments, the concentration of the solute in sample solution 30 is equal to the concentration of the solute in exchange chamber 18 when sample solution 30 and exchange chamber 18 reach equilibrium of solute concentrations.

According to embodiments, the measurement of sensor 22 is configured to correspond to the concentration of sample solution 30. Accordingly, the measurement taken by sensor 22 and the concentration of sample solution 30 may be expressed mathematically. The following is an example of how such a mathematical relationship may be determined in at least one embodiment. The concentration of sample solution 30 may be expressed as:

$$C_{sample} = C_{exhange}$$

$$C_{exchange} = n_{exchange}/V_{exchange}$$

where, "C" denotes a concentration, wherein "n" denotes the number of moles of solute, and "V" denotes a volume of the solution. Subscript designations throughout denote the reference area to which each symbol relates: "sample" for sample solution 30, "exchange" for exchange chamber 18, and "sensing" for sensing chamber 20. The formula above also applies to the concentration within exchange chamber 18:

In the above equation, $n_{exchange}$ is known and the volume of exchange chamber 18 is calculated from pressure measurements in sensing chamber 20. $n_{exchange}$ is known prior to implantation of device 10, either through direct measurement in a calibration step or by calculation based on known concentration and volume amounts prior to implantation of device 10. The amount of solute within exchange chamber 18 remains constant, and the change in concentration within exchange chamber 18 is attributed solely to a change in the amount of solvent. Because sample solution 30 and exchange chamber 18 are in fluid communication, the volume of exchange chamber 18 changes as solvent flows across filter membrane 14 and exchange chamber 18 reaches equilibrium with the concentration of sample solution 30.

For example, if device 10 is calibrated with a calibration solution, $n_{exchange}$ may be calculated by bringing exchange chamber 18 into equilibrium with the calibration solution. Because the concentration of the calibration solution is known and because the volume of exchange chamber may be calculated, $n_{exchange}$ may be calculated in a calibration step. For example:

$$n_{exchange} = \frac{[CalibrationSolution]}{V_{exchange}}$$

and $$V_{exchange} = V_{Device} - \left(\frac{P_{sensingI} V_{sensingI}}{P_{sensingF}}\right)$$

Thus, $$n_{exchange} = \left(\frac{[CalibrationSolution]}{V_{Device} - \left(\frac{P_{sensingI} V_{sensingI}}{P_{sendingF}}\right)}\right)$$

where $P_{sensingI}$ and $V_{sensingI}$ are the volume and pressure of sensing chamber taken prior to device 10 being placed into fluid communication with calibration solution, and $P_{sensingF}$ is the pressure of sensing chamber 20 after exchange chamber 18 has equilibrated with calibration solution.

As equilibrium is effected, the volume of exchange chamber 18 may change to accommodate the diffusion of solvent across filter membrane 14 into or out of exchange chamber 18. Separator 16 is be responsive to the diffusion of solvent across filter membrane 14 by repositioning (i.e., moving or expanding) to as the volume of exchange chamber 18 changes. The change of volume of exchange chamber 18 causes an equal and opposite change of volume of sensing chamber 20, which can be expressed as:

$$\Delta V_{exchange} = -\Delta V_{sensing}$$

Where the total combined volume of exchange chamber 18 and sensing chamber 20 are known before implantation of device 10, this equation can be expressed as:

$$V_{total} = V_{exchange} + V_{sensing}$$

where $V_{total}$ is the total combined volume of exchange chamber 18 and sensing chamber 20. $V_{total}$ is known and constant. Thus:

$$V_{total} = V_{exchange} + V_{sensing}$$

To determine changes in the volume of exchange chamber ($V_{exchange}$), pressure measurements are taken, according to embodiments, and the volume of sensing chamber is calculated, from which the volume of sensing chamber is determined. Because the amount of solute in sensing chamber is known, the concentration of exchange chamber is calculated. Thus, because exchange chamber 18 and sample solution 30 are in equilibrium, the concentration of sample solution 30, for example the concentration of glucose in body fluid, is known.

Sensing chamber 20 will have an initial (i) volume and pressure. After equilibrium is achieved with sample solution 30 and exchange chamber 18, sensing chamber will have a final (f) volume and pressure. Temperature calculations may be added to improve the accuracy. According to Boyle's Law:

$$P_i V_i = P_f V_f$$

Thus, the change in the volume of sensing chamber after equilibrium is established is calculated as:

$$V_f = \frac{P_i V_i}{P_f}.$$

The volume of exchange chamber 18 is then expressed as:

$$V_{exchange} = V_{Total} - V_f = V_{Total} - \left(\frac{P_i V_i}{P_f}\right).$$

Including temperature in the equation:

$$V_{exchange} = V_{Total} - V_f = V_{Total} - \left(\frac{P_i V_i T_f}{P_f T_i}\right).$$

The concentration is then calculated:

$$[ExchangeChamber] = \frac{n_{exchange}}{V_{exchange}}.$$

According to embodiments, device 10 is configured to determine instantaneous concentration of sample solution 30 before equilibrium of concentrations is achieved between sample solution 30 and exchange chamber 18. For example, the instantaneous rate of change of the volume of exchange chamber 18 may be used to determine the solute concentration of sample solution 30. The flux through filter membrane 14 may be proportional to the concentration gradient across filter membrane 14, wherein the flux is the amount of solvent that flows through a unit area of filter membrane 14 per unit time and the concentration gradient is the gradual difference in the concentration of solutes between sample solution 30 and exchange chamber 18. Stated differently, the concentration gradient changes at a rate proportional to that gradient. Thus, according to principles of calculus, this relationship is logarithmic, and the concentration gradient at any given time may be calculated based upon the rate of change, even before equilibrium is reached.

According to embodiments, device 10 is configured to determine physical conditions within a patient. In at least one embodiment, device 10 is configured to determine the glucose concentration within an interstitial fluid. For example, the solute may be glucose, and the solvent may be water, wherein exchange chamber contains a known amount of glucose in an aqueous solution of known volume. Filter membrane 14 may be an osmotic barrier to allow osmosis of water across filter membrane 14 to achieve equilibrium of concentrations between sample solution 30 and exchange chamber 18. Filter membrane 14 may further prohibit diffusion of glucose across filter membrane 14. Those skilled in the art will appreciate that other combinations of solutes and solvents may be applied to the present disclosure.

While the devices and method have been described in terms of what are presently considered to be the most practical and embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method comprising, providing a combination, the combination comprising:
   an exchange chamber;
   a sensing chamber containing a compressible fluid;
   a filter membrane configured to provide selective fluid communication between a sample solution and the exchange chamber when the filter membrane is in fluid communication with the sample solution, the filter membrane substantially impermeable to a solute contained in the exchange chamber;
   a movable separator configured to separate the exchange chamber from the sensing chamber; and
   a pressure sensor adapted to measure a pressure of the compressible fluid in the sensing chamber.

2. The method of claim 1, further comprising:
   providing a calibration sample of known concentration for determining an amount of solute in the exchange chamber.

3. The method of claim 1, further comprising providing instructions for using the combination to determine a physical condition within a patient.

4. The method of claim 3, wherein the instructions include implanting the combination in the patient's body.

5. The method of claim 3, wherein the instructions comprise putting the combination into contact with a bodily fluid of the patient such that the bodily fluid function as the sample solution.

6. The method of claim 5, wherein putting the combination into contact with a bodily fluid of the patient includes putting the combination into contact with interstitial fluid of the patient.

7. The method of claim 5, wherein the instructions comprise determining a glucose concentration in the bodily fluid.

8. The method of claim 5, wherein the instructions comprise determining the physical condition when a concentration of the solute in the exchange chamber reaches equilibrium with a concentration of the solute in the bodily fluid.

9. The method of claim 5, wherein the instructions comprise determining the physical condition prior to a concentration of the solute in the exchange chamber reaching equilibrium with a concentration of the solute in the bodily fluid the bodily fluid.

10. The method of claim 9, wherein determining the physical condition prior to the concentration of the solute in the exchange chamber reaching equilibrium with the concentration of the solute in the bodily fluid includes fitting a change in concentration of the solute in the exchange chamber to a curve of known behavior.

11. A method comprising:
    placing a solute concentration measurement device comprising a housing having disposed therein at least an exchange chamber, a sensing chamber containing a compressible fluid and having a pressure sensor adapted to measure a pressure of the compressible fluid, a filter membrane substantially impermeable to a solute in the exchange chamber and a movable separator disposed between the exchange chamber and the sensing chamber into fluid communication with a sample solution;

measuring the pressure of the compressible fluid in the sensing chamber; and using the measured pressure in the sensing chamber to calculate the concentration of the solute in the sample solution.

12. The method of claim 11, further comprising:

determining an amount of the solute in the exchange chamber prior to placing the solute concentration measurement device into fluid communication with the sample solution.

13. The method of claim 11, further comprising using the calculation of the concentration of the solute in the sample solution to determine a physical condition within a patient.

14. The method of claim 13, further comprising implanting the solute concentration measurement device in the patient's body.

15. The method of claim 13, wherein the sample solution is a bodily fluid of the patient.

16. The method of claim 15, wherein the bodily fluid of the patient is interstitial fluid of the patient.

17. The method of claim 15, wherein the solute is glucose and determining a physical condition within the patient includes determining a glucose concentration in the bodily fluid.

18. The method of claim 15, wherein the physical condition is determined when a concentration of the solute in the exchange chamber reaches equilibrium with a concentration of the solute in the bodily fluid.

19. The method of claim 15, wherein the physical condition is determined prior to a concentration of the solute in the exchange chamber reaching equilibrium with a concentration of the solute in the bodily fluid the bodily fluid.

20. The method of claim 19, wherein determining the physical condition prior to the concentration of the solute in the exchange chamber reaching equilibrium with the concentration of the solute in the bodily fluid includes fitting a change in concentration of the solute in the exchange chamber to a curve of known behavior.

* * * * *